US010345322B2

(12) United States Patent
Brueckner et al.

(10) Patent No.: US 10,345,322 B2
(45) Date of Patent: Jul. 9, 2019

(54) CARTRIDGE FOR STIRRING AND DISPENSING A FLUID, AUTOMATIC ANALYZER AND METHOD OF ANALYZING A BIOLOGICAL SAMPLE

(71) Applicant: Roche Diagnostics Operations, Inc., Indianapolis, IN (US)

(72) Inventors: Thorsten Brueckner, Schriesheim (DE); Christoph Boehm, Viernheim (DE); Juergen Spinke, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 299 days.

(21) Appl. No.: 15/138,474

(22) Filed: Apr. 26, 2016

(65) Prior Publication Data
US 2016/0252540 A1    Sep. 1, 2016

Related U.S. Application Data

(63) Continuation of application No. PCT/EP2014/069979, filed on Sep. 19, 2014.

(30) Foreign Application Priority Data

Oct. 31, 2013  (EP) .................................... 13191094

(51) Int. Cl.
*G01N 35/10*   (2006.01)
*B01F 7/00*    (2006.01)
(Continued)

(52) U.S. Cl.
CPC ..... *G01N 35/1016* (2013.01); *B01F 7/00141* (2013.01); *B01F 7/161* (2013.01);
(Continued)

(58) Field of Classification Search
CPC .................... G01N 2035/1058; B01F 15/0293
See application file for complete search history.

(56) References Cited

U.S. PATENT DOCUMENTS

| 1,764,498 A | 6/1930 | Beers |
| 3,583,682 A | 6/1971 | Berents |

(Continued)

FOREIGN PATENT DOCUMENTS

| CN | 1165559 A | 11/1997 |
| CN | 201434776 Y | 3/2010 |

(Continued)

OTHER PUBLICATIONS

International Search Report dated Mar. 11, 2015, in Application No. PCT/EP2014/069979, 6 pages.
(Continued)

*Primary Examiner* — Jill A Warden
*Assistant Examiner* — Dwayne K Handy
(74) *Attorney, Agent, or Firm* — Roche Diagnostics Operations, Inc.

(57) ABSTRACT

A cartridge for dispensing a fluid is provided, the cartridge comprising: a reservoir chamber configured for receiving the fluid, the reservoir chamber having a fluid outlet and a cover with a first bearing; and a stirring assembly comprising a stirrer located inside the reservoir chamber, the stirring assembly comprising a shaft connected to the stirrer. The stirring assembly can be moved between first and second positions, wherein in the first position the stirring assembly can seal the fluid outlet, the stirring assembly in the first position being configured to form a second bearing with the reservoir chamber or the fluid outlet such that the stirrer can be rotated about an axis defined by the first and second bearing, and wherein if the stirring assembly is in the second
(Continued)

position the fluid can pass through the fluid outlet, the shaft being configured to transmit rotational power to the stirrer.

14 Claims, 6 Drawing Sheets

(51) Int. Cl.
- *B01F 7/16* (2006.01)
- *B01F 13/10* (2006.01)
- *B01F 15/02* (2006.01)
- *B01L 3/00* (2006.01)
- *B01F 15/00* (2006.01)

(52) U.S. Cl.
CPC ........ *B01F 7/1695* (2013.01); *B01F 13/1072* (2013.01); *B01F 15/00993* (2013.01); *B01F 15/027* (2013.01); *B01F 15/0292* (2013.01); *B01L 3/502* (2013.01); *B01F 2015/0011* (2013.01); *B01F 2015/00103* (2013.01); *B01L 2300/04* (2013.01); *B01L 2300/042* (2013.01); *B01L 2300/046* (2013.01); *B01L 2300/0832* (2013.01); *B01L 2300/0851* (2013.01); *B01L 2400/0475* (2013.01); *B01L 2400/0633* (2013.01); *G01N 2035/1058* (2013.01)

(56) References Cited

U.S. PATENT DOCUMENTS

| | | | |
|---|---|---|---|
| 4,277,184 A * | 7/1981 | Solomon | A61B 17/8822 366/139 |
| 4,499,562 A | 2/1985 | Campolini et al. | |
| 5,797,679 A * | 8/1998 | Grulke | B01F 7/18 366/139 |
| 6,042,262 A * | 3/2000 | Hajianpour | A61B 17/8822 366/139 |
| 7,160,020 B2 * | 1/2007 | Sand | B01F 7/0005 366/139 |
| 9,808,775 B2 * | 11/2017 | Sasaki | B01F 7/00408 |
| 2007/0036684 A1 * | 2/2007 | Burkhardt | B01L 3/5027 422/400 |
| 2008/0085507 A1 | 4/2008 | Stroud et al. | |
| 2011/0249526 A1 | 10/2011 | Wong | |
| 2012/0118919 A1 | 5/2012 | Cianciolo | |
| 2012/0149007 A1 * | 6/2012 | Abrams | A61B 5/15186 435/5 |
| 2012/0155216 A1 | 6/2012 | Morrissey et al. | |

FOREIGN PATENT DOCUMENTS

| | | |
|---|---|---|
| CN | 102109528 A | 6/2011 |
| EP | 1959257 A2 | 8/2008 |
| GB | 2120115 A | 11/1983 |
| JP | H04-166768 A | 6/1992 |
| JP | H05-279047 A | 10/1993 |
| JP | H06-002738 Y2 | 1/1994 |
| SU | 1668154 A1 | 8/1991 |
| WO | 2013/167209 A1 | 11/2013 |

OTHER PUBLICATIONS

Office Action dated Jun. 6, 2018, in Japanese Application No. 2016-550964, 3 pp.

\* cited by examiner

CARTRIDGE FOR STIRRING AND DISPENSING A FLUID, AUTOMATIC ANALYZER AND METHOD OF ANALYZING A BIOLOGICAL SAMPLE

CROSS-REFERENCE TO RELATED APPLICATIONS

This application is a continuation of International Patent Application No. PCT/EP2014/069979, filed 19 Sep. 2014, which claims the benefit of European Patent Application No. 13191094.5, filed 31 Oct. 2013, the disclosures of which are hereby incorporated by reference in their entirety.

TECHNICAL FIELD

The present disclosure relates to the analysis of biological samples and, in particular, to cartridges for dispensing microfluidic portions of fluids for the purpose of performing an analysis of a biological sample.

BACKGROUND

In medical laboratories, in vitro diagnostics are commonly performed on biological samples. Such tests may be performed manually using pipettes or may be performed using an automatic analyzer. Automatic analyzers may automatically add reagents to the biological sample in order to determine the amount of a substance in the biological sample.

For some analysis procedures one of the reagents used for the analysis may be a fluid comprising microparticles. When storing such a fluid in a container, the microparticles will tend to sediment on the bottom of the container due to their higher specific gravity compared to the specific gravity of the fluid. Before the fluid can be used for analysis purposes the microparticles have to be brought back into a suspended and homogeneous state, such that a well-defined amount of microparticles can be dispensed with a defined amount of fluid. One possible way to resuspend sedimented microparticles is to stir the fluid containing the microparticles.

BRIEF SUMMARY

It is against the above background that the embodiments of the present disclosure provide certain unobvious advantages and advancements over the prior art. In particular, the inventors have recognized a need for improvements in methods to perform a measurement of an analyte in a sample using an automatic analyzer, and a cartridge assembly.

In accordance with one embodiment of the disclosure, a cartridge for dispensing a fluid is provided, wherein the cartridge comprises: a reservoir chamber configured for receiving the fluid, the reservoir chamber having a fluid outlet, wherein the reservoir chamber further comprises a cover with a first bearing; a stirring assembly comprising a stirrer located inside the reservoir chamber, the stirring assembly further comprising a shaft, the shaft being connected to the stirrer, the shaft further being located at least partially inside the reservoir chamber and the shaft being configured to transmit rotational power to the stirrer, wherein the stirring assembly is configured to be moved between a first position and a second position, wherein in the first position the stirring assembly is operable to seal the fluid outlet, the stirring assembly in the first position further being operable to form a second bearing with the reservoir chamber or the fluid outlet such that the stirrer can be rotated about an axis defined by the first and second bearing, and wherein if the stirring assembly is in the second position the fluid can pass through the fluid outlet.

In accordance with another embodiment of the disclosure, an automatic analyzer for analyzing a biological sample is provided, the automatic analyzer comprising a holder for holding a cartridge in accordance with the present disclosure, the automatic analyzer further comprising a first actuator assembly operable for actuating a controllable dispenser component for controlling the controllable dispenser component to dispense the dispensing volume from the cartridge, the automatic analyzer being operable to perform an analysis of the biological sample for detecting an analyte using the dispensing volume, the automatic analyzer further comprising a driving assembly configured to rotate the stirring assembly, and to move the stirring assembly between the first and the second position.

In accordance with yet another embodiment of the present disclosure, a method for stirring and dispensing a fluid from a cartridge in accordance with the present disclosure is provided, the method comprising: moving the stirring assembly to the first position, applying rotational power onto the shaft of the stirring assembly, moving the stirring assembly to the second position, and dispensing a dispensing volume of fluid from the cartridge.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1B:
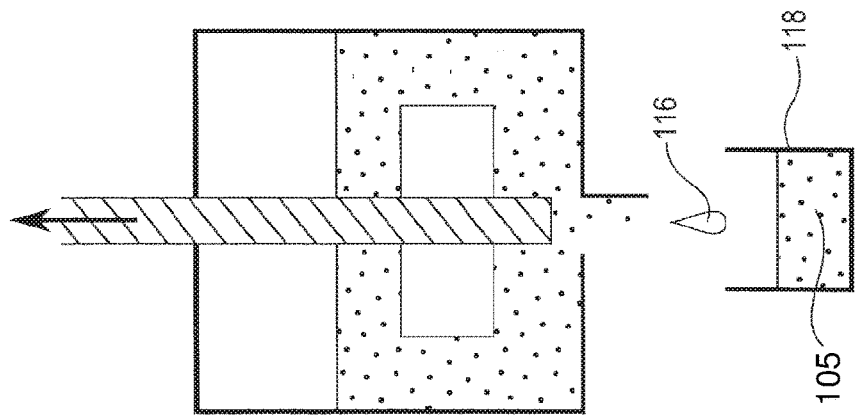
FIG. 1B is a schematic of a cartridge according to an embodiment of the present disclosure, wherein the stirring assembly is in its second position.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

In accordance with embodiments of the present disclosure a cartridge comprises a reservoir chamber configured for receiving a fluid. The reservoir chamber may for example be made of but is not limited to polyethylene, polypropylene or any other material that is compatible with the fluid contained within the reservoir chamber. The reservoir chamber has a fluid outlet and a cover with a first bearing. The cover may be designed such that it is operable to seal the reservoir chamber from surrounding air and may be removable from the reservoir chamber. Removing the cover from the reservoir chamber may be used in order to fill the reservoir chamber with the fluid. For example, the cover may be designed as a screw cap or may be affixed to the reservoir chamber using a clamping device or other fastening means. The first bearing of the cover may, for example, be a magnetic bearing, a friction bearing, a ball bearing or any other type of bearing suitable for the use of the first bearing as described below.

The cartridge further comprises a stirring assembly comprising a stirrer and a shaft wherein the stirrer is located inside the reservoir chamber. The shaft is connected to the stirrer thereby being configured to transmit rotational power to the stirrer. As a result the stirring assembly is configured to stir the fluid inside the reservoir chamber to re-suspend particles comprised within the fluid. The shaft is located at least partially inside the reservoir chamber. The stirring assembly formed by the stirrer and the shaft is configured to move between a first and a second position.

In some embodiments the first position may correspond to a first axial position of the stirring assembly, and the second position may correspond to a second axial position of the stirring assembly. Alternatively or in combination, the first position may also correspond to a first angular range of rotation of the stirring assembly, while the second position corresponds to a second angular range of rotation of the stirring assembly.

When the stirring assembly is in the first position the stirring assembly seals the fluid outlet. To this end the stirrer or the shaft of the stirring assembly may, for example, protrude into the fluid outlet thereby forming a form lock fixing with the fluid outlet of the reservoir chamber. Alternatively, the fluid outlet may also be opened or sealed by rotating the stirring assembly to predefined angular ranges while the stirring assembly protrudes into the fluid outlet. To this end the stirring assembly and the fluid outlet or the reservoir chamber itself may comprise grooves, which when brought into alignment at least partially, form a channel, enabling the fluid to flow out of the reservoir chamber.

While protruding into the fluid outlet of the reservoir chamber the stirring assembly is operable to form a second bearing with the reservoir chamber and/or the fluid outlet such that the stirrer can be rotated about an axis defined by the first and second bearing. As a result the stirring assembly is configured to stir the fluid inside the reservoir chamber to re-suspend particles comprised within the fluid when in the first position. The second bearing may, for example, comprise a thermoplastic elastomer or any other material suitable for forming a friction sealing.

In some embodiments the stirring assembly may seal the fluid outlet by protruding into the fluid outlet of the reservoir chamber.

When the stirring assembly is in the second position the fluid outlet is no longer sealed and thus fluid can be dispensed from the cartridge. Switching the stirring assembly between the first and second position may, for example, correspond to raising or lowering the stirring assembly inside the reservoir chamber. Once the stirring assembly is lowered the stirrer or the shaft of the stirring assembly may extend into the fluid outlet thereby sealing it. Raising the stirring assembly may remove the shaft or the stirrer from the fluid outlet thereby opening the fluid outlet such that a fluid can be dispensed.

Embodiments of the disclosure may be advantageous for storing and dispensing a fluid being a suspension or dispersion containing particles that sediment on a bottom portion of the cartridge. Prior to dispensing a portion of the fluid for the purpose of performing an analysis, the sedimented particles or at least a portion of the sedimented particles are suspended by stirring the fluid using a stirring assembly. By stirring the fluid with an appropriate rotational frequency for the stirrer and for an appropriate period of time, the sedimented particles are mixed with the fluid such that the particles are put back into suspended state. In other words, the sedimented particles are resuspended by stirring the fluid using the stirring assembly. This may have the advantage that the concentration and distribution of the particles in the fluid fraction of the suspension reaches a predefined level before the dispensing volume is dispensed from the cartridge for the purpose of performing an analysis. This ensures that the analysis can be performed with a reproducible degree of precision.

Embodiments of the disclosure may further have the advantage that the stirring assembly is designed as an integral part of a cartridge. Thus the stirring assembly is only used for the fluid inside this single cartridge and will not come into contact with other fluids contained within other cartridges. Using the stirrer only for a single fluid instead of a plurality of fluids prevents contamination of the fluids, which may occur if the stirrer is not cleaned properly after stirring a different fluid. In addition, it may not be necessary to clean the stirring assembly after a stirring process, which may otherwise reduce the turnaround time of an analysis cycle.

Further, the cartridge according to the embodiment may remain sealed from surrounding air for multiple mixing and dispensing cycles, thereby preventing air from getting into the cartridge, which might cause deterioration of the fluid contained within the cartridge.

Another advantage of the embodiment described above may be that the stirring assembly is used for the purpose of stirring the fluid contained within the cartridge, as well as for sealing and opening the fluid outlet of the cartridge. Thus, no additional valve for sealing and opening the fluid outlet during a dispensing process and no additional means for controlling the operation of such a valve are necessary. Further, the use of the stirring assembly as a sealing means facilitates the transfer of cartridges since they can be sealed easily without any further means.

A "cartridge" as understood herein comprises a receptacle for storing and dispensing a fluid. The cartridge may have a mechanical interface that matches the mechanical interface of a holder of an automatic analyzer. The mechanical interfaces of the cartridge and the automatic analyzer may enable mounting and releasing of the cartridge to and from the holder of an analyzer such that the cartridge can be conveniently replaced by a new cartridge when the cartridge is empty.

In some embodiments the first bearing is formed by a portion at a first end of the stirring assembly and a portion of the cover. For example, the first end of the stirring assembly as well as the portion of the cover may comprise magnetic elements thereby forming a magnetic bearing. The portion of the cover may also be designed such that it forms guidance for the first end of the stirring assembly wherein the first end of the stirring assembly and/or the portion of the cover may be coated with a material suitable for use in a slide bearing and may be formed for example using 2k injection molding. The coating material may be chosen such that friction within the bearing is reduced. For example, the first end of the stirring assembly and the portion of the cover may be coated with an anti-friction agent like a modified thermoplastic elastomer (TPE) or comparable synthetic materials. In some embodiments the portion at the first end of the stirring assembly and the portion of the cover are designed such that they receive or form a ball bearing as the first bearing. When coating the parts of the bearings care should be taken when choosing the coating material. Since the operation of a friction bearing typically bears the risk of producing wear debris that may get into the fluid contained within the cartridge, the coating material should be chosen such that even if some of the coating material gets into the fluid no detrimental contamination of the fluid is caused.

Yet another possibility to form the first bearing is to provide a hole in the cover such that the shaft of the stirring assembly can project through the hole and can form a slide bearing with the sidewalls of the hole. However, care should be taken that the first bearing is designed such that no surrounding air can get into the cartridge as this may cause deterioration of the fluid.

The second bearing is formed by a surface at a second end of the stirring assembly and a surface of the reservoir chamber or the fluid outlet. The type of bearing can be chosen such that it is suitable for sealing the reservoir chamber if the stirring assembly is in the first position. For example, one may use a slide bearing.

In some embodiments of the disclosure the cover of the reservoir chamber is configured to seal an opening of the reservoir chamber as described before herein. The cover itself may be designed such that it extends along the shaft, for example by protruding into the reservoir chamber thereby reducing the volume of the chamber. Further, the cover may have an opening configured to receive the shaft of the stirring assembly. This corresponds to the case in which the first bearing is formed by the sidewall of an opening of the cover and the stirring assembly as described before herein. By designing the cover such that it extends along the shaft and has an opening for receiving the shaft, the opening of the cover forms an axially elongate radial bearing for the shaft. For example, the cover and the respective opening may be designed such that it forms a bearing half the length of the shaft of the stirring assembly. However, the bearing may also be designed such that it covers four fifth or less, three fourth or less, half or less, one fourth or less, one fifth or less, one eighth or less, or one tenth or less the length of the shaft.

It should be noted that an axially elongate bearing may not only be achieved by designing the cover such that it protrudes into the reservoir chamber. It is also possible to design the cover such that it forms a camber pointing away from the reservoir chamber thereby forming a bearing for a part of the shaft being located outside the reservoir chamber. However, in some embodiments the cover may protrude into the reservoir chamber, such that the distance between the fluid outlet and the opening of the cover is less than the distance between the fluid outlet and the opening of the reservoir chamber.

Using an axially elongate bearing as a channel-like guidance for the shaft of the stirring assembly may have the advantage that the mechanical stability of the stirring assembly is increased, especially when in the first position. Tilting of the stirring assembly if a force in radial direction impinges onto parts of the stirring assembly, which may cause jamming of the stirring assembly, may be prevented.

In some embodiments the stirring assembly comprises a venting channel configured to form a first and second opening when the stirring assembly is in its second position. The first opening is located outside the reservoir chamber when the stirring assembly is in its second position, while the second opening is located inside the reservoir chamber when the stirring assembly is in its second position. As a result a connection between the interior of the reservoir chamber and the surrounding air can be formed when the stirring assembly is in its second position, thereby enabling ventilation of the reservoir chamber when the stirring assembly is in its second position. A venting channel may be advantageous if the fluid is to be dispensed from the cartridge, for example, by simply opening the fluid outlet. If no venting channel is provided a vacuum may evolve in an upper portion of the cartridge thereby preventing fluid from passing through the fluid outlet. Thus, providing a venting channel may facilitate the dispensing procedure especially if no controllable dispenser component, which may provide suction, is used.

However, the cartridge may also be designed such that dispensing a dispensing volume from the cartridge without a venting channel and without the use of means generating suction onto the fluid is possible. For example, the amount of air within the cartridge relative to the amount of fluid within the cartridge can be chosen such that dispensing a dispensing volume of fluid does not cause the air pressure above the fluid to drop to a value preventing the dispensing volume from getting out of the cartridge. Further, it may be possible to generate excess pressure within the reservoir chamber when filling the reservoir chamber with the fluid.

In some embodiments the stirring assembly may comprise a venting channel, the venting channel extending from an outside portion of the stirring assembly outside the reservoir chamber to an inside portion of the stirring assembly inside the reservoir chamber.

In accordance with an embodiment of the disclosure the venting channel is sealed if the stirring assembly is in the first position and the venting channel is open if the stirring assembly is in the second position. This may be advantageous as a venting channel is only necessary if a dispensing volume of the fluid is to be dispensed from the cartridge. In accordance with embodiments of the disclosure dispensing a dispensing volume from the cartridge is only possible if the stirring assembly is in the second position. Therefore, the venting channel is automatically opened when preparing the cartridge for dispensing a fluid by moving the stirring assembly to the second position. It is also possible to design the ventilation opening such that the venting channel is sealed if the stirring assembly is rotated to a first angular range and wherein the venting channel is open if the stirring assembly is rotated to a second angular range. It is also possible to combine the embodiments described above.

Designing the venting channel as described above may have the advantage that the venting channel is realized using elements that are part of the cartridge either way and thus no additional elements are necessary. Further, the operation of such a venting channel can be controlled using an assembly that is configured to rotate the stirring assembly and to move the stirring assembly between the first and second position. Thus, no additional elements are necessary to provide and control ventilation of the cartridge.

In some embodiments the stirrer may be one of an Archimedean screw, a paddle mixer, a propeller mixer, a spiral mixer, or an impeller mixer. When choosing the design of the stirrer care should be taken that the stirrer does not damage a coating of the particles comprised in the fluid or the particles themselves when stirring the fluid. Damage may be caused, for example, due to shear strain caused by the stirrer. Besides the shape of the stirrer, the rotational frequency of the stirrer when stirring the fluid should be chosen carefully as well.

In some embodiments the cartridge further comprises a controllable dispenser component for dispensing a dispensing volume of the fluid from the reservoir chamber, wherein the dispenser component is connected to the fluid outlet of the reservoir chamber. The dispenser component is operable for receiving the fluid from the outlet of the reservoir chamber and subsequently releasing the fluid upon being actuated. A dispenser component in accordance with embodiments of the disclosure may be controllable in that the amount of fluid dispensed, the timing of dispensing as well as the time period for the dispensing process can be controlled. For example, a dispenser may comprise a cylinder and a piston connected to the fluid outlet. To draw fluid from the cartridge the piston may be moved away from the fluid outlet, thereby producing a vacuum such that a dispensing volume of the fluid contained within the reservoir chamber is drawn into the cylinder. To dispense the fluid from the dispenser component, the piston may be moved back towards the fluid outlet of the cartridge, thereby affecting pressure onto the fluid inside the cylinder. To ensure that the dispensing volume is dispensed and not simply put back into the reservoir chamber a valve may be used. This valve functionality can also be provided by the stirring assembly when the stirring assembly is in its second position. As a result the dispensing volume of the fluid will be forced out of the dispenser component. However, other embodiments of a dispenser component may be used as well.

In some embodiments the dispenser may be a microfluidic dispenser for dispensing a microfluidic portion of the fluid. In other embodiments the dispenser may comprise a nozzle. For instance, the dispenser may comprise a straight tube or may comprise a nozzle with one or more valves contained within it.

In accordance with another embodiment, the disclosure provides an automatic analyzer for analyzing biological samples. The automatic analyzer comprises a holder configured for holding a cartridge as described above, wherein the holder is typically designed such that it can receive or release a cartridge. The automatic analyzer further comprises a first actuator assembly operable for actuating a controllable dispenser component. The controllable dispenser component is used to dispense the dispensing volume from the cartridge and can be an integral part of the cartridge itself or can be a part of the analyzer. Using the dispensing volume the automatic analyzer is configured to perform an analysis of a biological sample for detecting an analyte as described below. The automatic analyzer further comprises a driving assembly configured to rotate the stirring assembly and to move the stirring assembly between the first and the second position. To this end the driving assembly is typically designed such that it can be connected to the shaft of the stirring assembly of the cartridge.

The dispenser component and the stirring assembly may be mechanically, pneumatically, magnetically, and/or electrically actuated. This is dependent upon the implementation and how the dispenser is constructed. In an embodiment the cartridge is in an operating position when installed into the automatic analyzer.

In some embodiments the automatic analyzer may further comprise a controller, the controller being programmed to:
control the driving assembly to move the stirring assembly to the first position,
control the driving assembly to rotate the stirring assembly,
control the driving assembly to move the stirring assembly to the second position,
control the first actuator assembly to dispense the dispensing volume of the fluid.

A "controller" as used herein encompasses a device, machine, or apparatus for controlling the operation and/or function of one or more other devices. Examples of a controller may include, but are not limited to: a computer, a processor, an imbedded system or controller, a programmable logic controller, and a microcontroller. A 'computing device' or 'computer' as used herein encompasses any device comprising a processor. A 'processor' as used herein encompasses an electronic component that is able to execute a program or machine executable instruction.

In yet another embodiment a method for stirring and dispensing a fluid from a cartridge according an embodiment described above is provided, the method comprising the steps of:
moving the stirring assembly to the first position,
applying rotational power onto the shaft of the stirring assembly,
moving the stirring assembly to the second position,
dispensing a dispensing volume of fluid from the cartridge.

It is understood that one or more of the aforementioned embodiments of the disclosure may be combined as long as the combined embodiments are not mutually exclusive. In order that the embodiments of the present disclosure may be more readily understood, reference is made to the following examples, which are intended to illustrate the disclosure, but not limit the scope thereof.

Figure 1A:
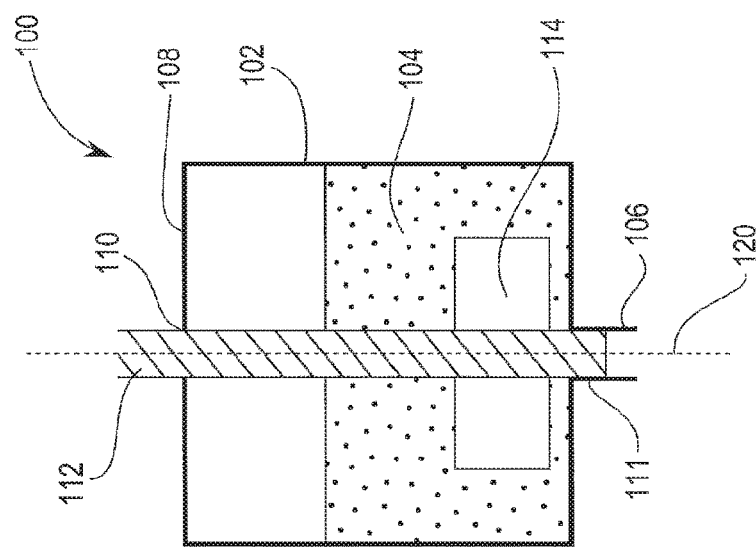
FIG. 1A is a schematic of a cartridge according to an embodiment of the present disclosure, wherein the stirring assembly is in its first position.

FIGS. 1A and 1B illustrate an example of a cartridge 100 with the stirring assembly in two different positions. The cartridge shown in the two figures will be described herein with reference to FIG. 1A.

The cartridge 100 shown in FIG. 1A comprises a reservoir chamber 102 configured for holding a fluid 104. The cartridge 100 further comprises a fluid outlet 106 being located in a lower portion of the reservoir chamber 102 as well as a cover 108 designed for closing the reservoir chamber 102. The cover 108 has an opening that forms a first bearing 110 for a shaft 112 extending through the opening. A stirrer 114 is mounted on the shaft 112 such that the stirrer 114 is at least partly submerged into the fluid 104. The shaft 112 and the stirrer 114 form a stirring assembly. In the embodiment depicted in FIG. 1A, the shaft 112 of the stirring assembly extends into the fluid outlet 106 of the cartridge 100. As a result the fluid outlet 106 forms a second bearing 111 for the shaft 112. The first bearing 110 and the second bearing 111 define a rotational axis 120 for the shaft 112.

The embodiment depicted in FIG. 1A has been previously described herein as a first position of the stirring assembly. In this first position the shaft 112 of the stirring assembly extends into the fluid outlet 106 thereby sealing the reservoir chamber 102 such that no fluid 104 can leak from the cartridge 100. Further, the first and second bearing 110 and 111 define a rotational axis 120 for the shaft 112 such that the stirrer 114 can be rotated about the rotational axis 120, for example, by applying a torque onto the shaft 112. Thus, the stirring assembly can be used to stir the fluid 104 contained in the reservoir chamber 102 if the stirring assembly is in the first position as depicted in FIG. 1A.

In the embodiment depicted in FIG. 1B, the stirring assembly has been moved in an upward direction such that the shaft 112 of the stirring assembly no longer extends into the fluid outlet 106. As described before herein, the stirring assembly is now in a second position. Since the shaft 112 of the stirring assembly no longer extends into the fluid outlet 106 a dispensing volume 116 of the fluid 104 may now be dispensed from the reservoir chamber 102. According to embodiments of the disclosure the dispensing volume 116 of a reagent fluid 104 contained within the reservoir chamber 102 is added to and mixed with a biological sample 105 contained in a receptacle 118 located below the cartridge 100 for performing an analysis in order to detect an analyte.

Once a sufficient amount of fluid 104 has been dispensed from the cartridge 100 the stirring assembly can be moved back to the first position depicted in FIG. 1A such that the fluid outlet 106 is sealed by the shaft 112. The stirring assembly may then be actuated again for stirring the fluid 104 in preparation of a subsequent dispensing procedure.

It should be noted that the first and second position of the stirring assembly depicted in FIGS. 1A and 1B are only one example for first and second positions of a stirring assembly in accordance with the disclosure. Another example for first and second positions of the stirring assembly will be given with reference to FIGS. 3A-3E.

Figure 2:
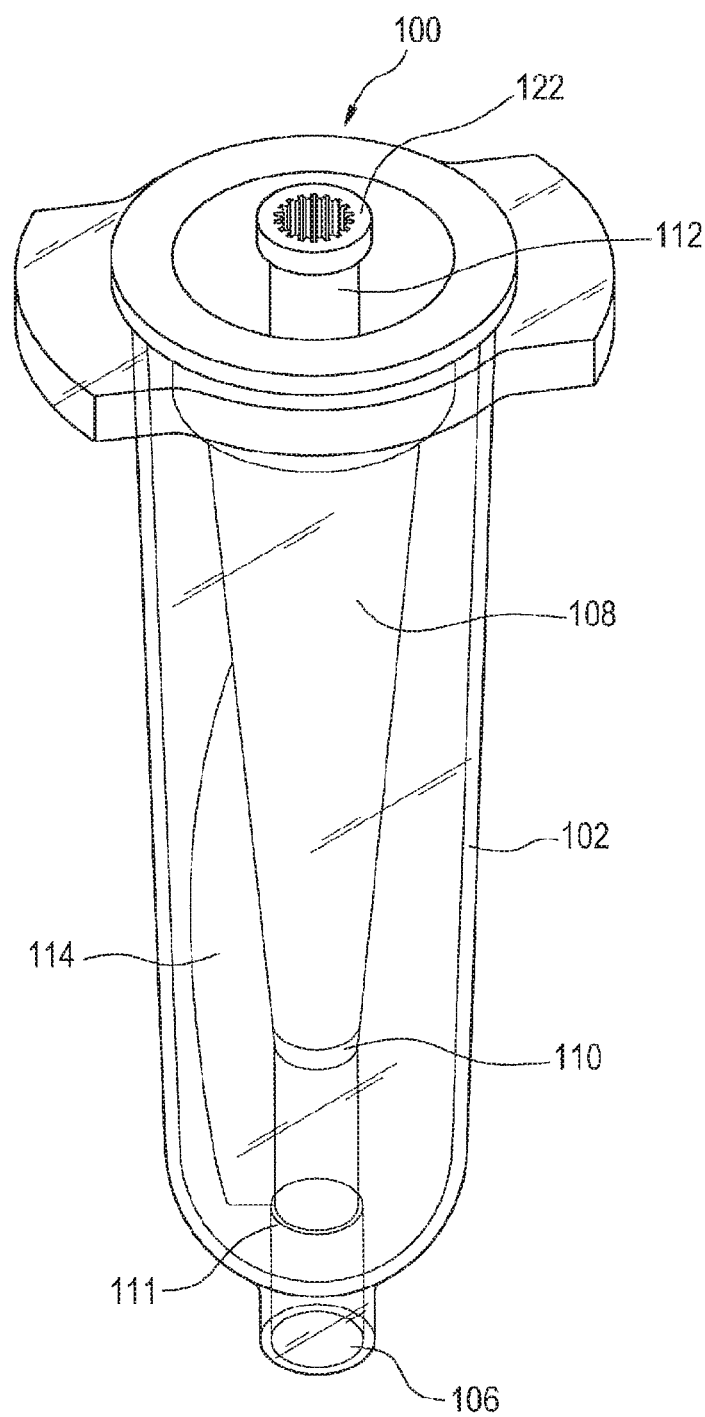
FIG. 2 is an illustration of a cartridge with a cover extending into the reservoir chamber in accordance with an embodiment of the present disclosure.

FIG. 2 is an illustration of a cartridge 100 with a cover 108 extending into the reservoir chamber 102, thereby reducing the volume of the reservoir chamber 102. In an upper portion of the cover 108 the shaft 112 projects out of the cover 108. A top portion of the shaft 112 forms an adapter 122, which will be described in more detail herein with reference to FIG. 4. The adapter 122 is designed such that an external driving entity can be connected to the shaft 112 such that the driving entity can transmit rotational power to the stirrer 114. As a result the external driving entity is enabled to rotate the stirrer 114.

As mentioned before herein, the cover 108 extends into the reservoir chamber 102. As a result the distance between the first bearing 110 formed by the shaft 112 and the cover 108 from the second bearing 111 formed by the fluid outlet 106 and the shaft 112 or the stirrer 114 is reduced. This increases the mechanical stability of the stirring assembly if the stirring assembly is in the second position and the shaft 112 does no longer extend into the fluid outlet 106.

The mechanical stability of the stirring assembly can be improved further by designing the cover 108 such that the cover 108 forms a guiding for the shaft 112. For example, the cover 108 may be designed such that the first bearing 110 extends all the way from the lower point near the fluid outlet where the shaft 112 enters the opening of cover 108 to the upper portion of the cover where the shaft 112 projects out of the cover 108. As a result a tunnel-like bearing can be formed by the opening of the cover, preventing the stirring assembly from tilting or even jamming if a force in radial direction impinges onto the stirring assembly.

When dispensing a part of the fluid 104 contained within the reservoir chamber 102, one may have to provide some sort of ventilation to the reservoir chamber to enable a flow of fluid 104 from the cartridge 100, especially if no dispensing component using suction is used. If no ventilation is provided to the reservoir chamber a partial vacuum may evolve in the reservoir chamber 102 thereby preventing fluid 104 from being dispensed from the cartridge 100.

Figure 3A:
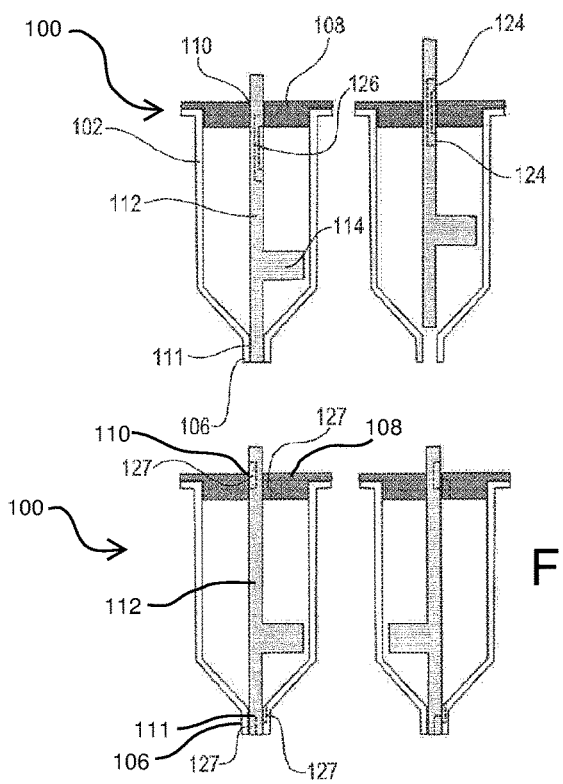
FIGS. 3A-3E are schematics of possible ventilation and outlet sealing mechanisms in accordance with embodiments of the present disclosure.
Figure 3B:
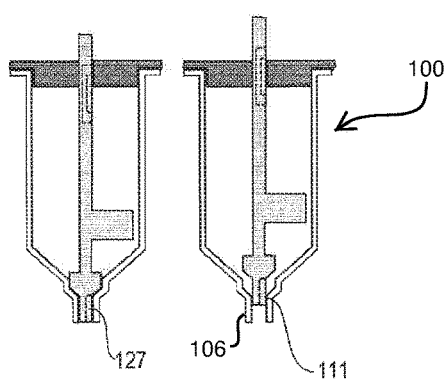
Figure 3C:
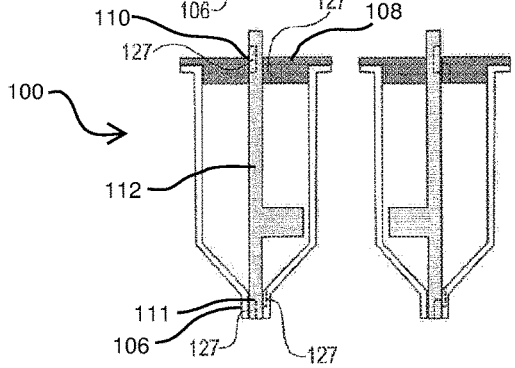

FIGS. 3A-3E are schematics of different ventilation as well as outlet sealing mechanisms. For example, FIG. 3A shows a reservoir chamber 102 that is sealed by a cover 108. The cover 108 has a hole configured to receive the shaft 112 of the stirring assembly, thereby forming a first bearing 110 for the shaft. Further, the outlet 106 of the reservoir chamber 102 is configured to receive the shaft 112. The outlet 106 of the reservoir chamber 102 is designed such that it is sealed once the shaft 112 protrudes into the outlet 106. Further, the outlet 106 is configured to form a second bearing 111 with the shaft 112. The stirring assembly of the cartridge shown in FIGS. 3A-3C is formed by the shaft 112 and the stirrer 114.

The shaft 112 of the stirring assembly further comprises a ventilation channel 126, extending in an axial direction along the shaft 112, with two openings 124. In the embodiment depicted in FIG. 3A, the first and second position of the stirring assembly correspond to a lower position (first) and an upper position (second). In the lower position the shaft 112 protrudes into the outlet 106 and can be rotated about an axis defined by the first 110 and second 111 bearing. While in the lower position the openings 124 of the venting channel 126 are both below the upper surface of the cover 108. As a result there is no connection between the interior of the reservoir chamber 102 and its surroundings and no air can flow into or out of the cartridge 100. It should be noted that the upper opening 124 does not necessarily have to be located within the bearing 110 of the cover 108. It may as well be located completely below the cover 108.

When the stirring assembly is in the upper position, the shaft 112 does not seal the fluid outlet 106 anymore. Further, the venting channel 126 is now located such that the upper opening 124 is located outside the reservoir chamber 102, while the lower opening 124 is located inside the reservoir chamber 102. As a result a channel is formed, which enables air to flow into the cartridge 100, thereby avoiding a vacuum to emerge in the reservoir chamber 102 upon dispensing a fluid from the cartridge 100.

It should also be noted that the venting channel formed by the channel 126 with the two openings 124 does not necessarily have to be formed as a tunnel-like channel inside the shaft 112 as shown in FIGS. 3A and 3B. It may also be possible to achieve a venting mechanism that is mostly the same as the mechanism shown in FIGS. 3A and 3B by cutting a groove approximately the same length as the channel 126 into the shaft 112.

FIG. 3B shows another embodiment of a cartridge. In this embodiment the ventilation mechanism is comparable to the ventilation mechanism described herein with reference to FIG. 3A. However, the embodiment of FIG. 3B differs from the embodiment of FIG. 3A in that the fluid outlet 106 is designed differently and in another outlet mechanism. The outlet 106 is designed as a cone and a lower portion of the shaft 112 forms a corresponding counterpart. As a result sealing the fluid outlet 106 is facilitated as it can be achieved by forcing the cone shaped counterpart of the shaft 112 into the coneshaped part of the fluid outlet 106. In addition to this advantageous outlet design the outlet mechanism differs from the mechanism described herein with reference to FIG. 3A. According to FIG. 3B the first and second positions of the stirring assembly again correspond to an upper and lower position of the stirring assembly. While the lower position of the stirring assembly is mostly the same as in FIG. 3A, the upper position of stirring assembly differs from FIG. 3A in that even in the second position the shaft 112 of the stirring assembly still protrudes into the outlet 106. This may have the advantage that rotating the stirring assembly while in the upper position bears a reduced risk of jamming the stirring assembly, as the shaft 112 of the stirring assembly is still guided by two bearings 110, 111 instead of the single upper bearing 110.

However, as even in the second position the shaft 112 of the stirring assembly still protrudes into the fluid outlet 106, the outlet mechanism is changed with respect to FIG. 3A. To this end the shaft 112 of the stirring assembly comprises at least a groove 127 designed such, that while the stirring assembly is in the upper position a channel is formed by the groove 127 and the outlet 106 and/or the reservoir chamber 102 such that a fluid can be dispensed from the cartridge 100. It should be noted that the outlet mechanism of FIG. 3B may be used with the cartridge 100 of FIG. 3A as well.

The cartridge 100 shown in FIG. 3C shows yet another type of venting as well as outlet mechanism. In the cartridge depicted in FIG. 3C the first and second position of the stirring assembly are no longer an upper or lower position but defined angular ranges of the stirring assembly. To this end the shaft 112 comprises at least two grooves: one in an upper part of the shaft 112 in the region of the first bearing 110 and one in a lower part of the shaft 112 in the region of the second bearing 111. Further, the cover 108 as well as the fluid outlet 106 comprise grooves 127 as counterparts to the grooves 127 of the shaft 112.

Figure 3D:
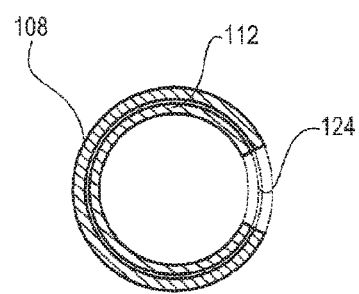
Figure 3E:
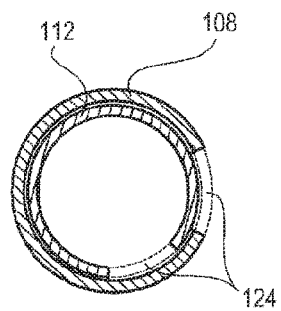

The left illustration of FIG. 3C shows the cartridge 100 in its first state. As can be seen the grooves 127 of the shaft 112 and the grooves 127 of cover 108 and fluid outlet 106 are out of alignment, as for example illustrated further in FIG. 3E in a top view. Since the grooves 127 are out of alignment it is neither possible to dispense a fluid from the cartridge 100, since the fluid outlet 106 is sealed, nor is it possible to ventilate the cartridge 100. The right illustration of FIG. 3C shows the cartridge in the second position as the shaft has now been rotated such that the grooves 127 of shaft 112, cover 108 and fluid outlet 106 are at least partially matching. This situation is depicted in FIG. 3D as well in a top view. As the grooves 127 are now matching, a portion of fluid can be dispensed from the cartridge, while at the same time the cartridge 100 can be ventilated thereby facilitating the dispensing procedure.

The embodiment depicted in FIG. 3C may be particularly advantageous, as no axial motion of the stirring assembly is necessary to open or seal the cartridge. Therefore, the driving assembly for actuating the stirring assembly only has to provide a rotational and no axial movement and thus can be kept simple. Further, the stirring assembly is guided by both bearings 110 and 111 at all times, which may prevent jamming of the stirring assembly caused by forces impinging onto the stirring assembly in a radial direction. While stirring a fluid contained within the cartridge 100, the ventilation opening as well as the outlet of the cartridge are repeatedly opened and closed. However, if the dispensing step is carried out using an attached dispensing element as, for example, shown in FIG. 5, this should not bear the risk of leakage of the fluid from the cartridge during the stirring procedure as the dispensing element may comprise a further sealing or valve functionality.

Figure 4:
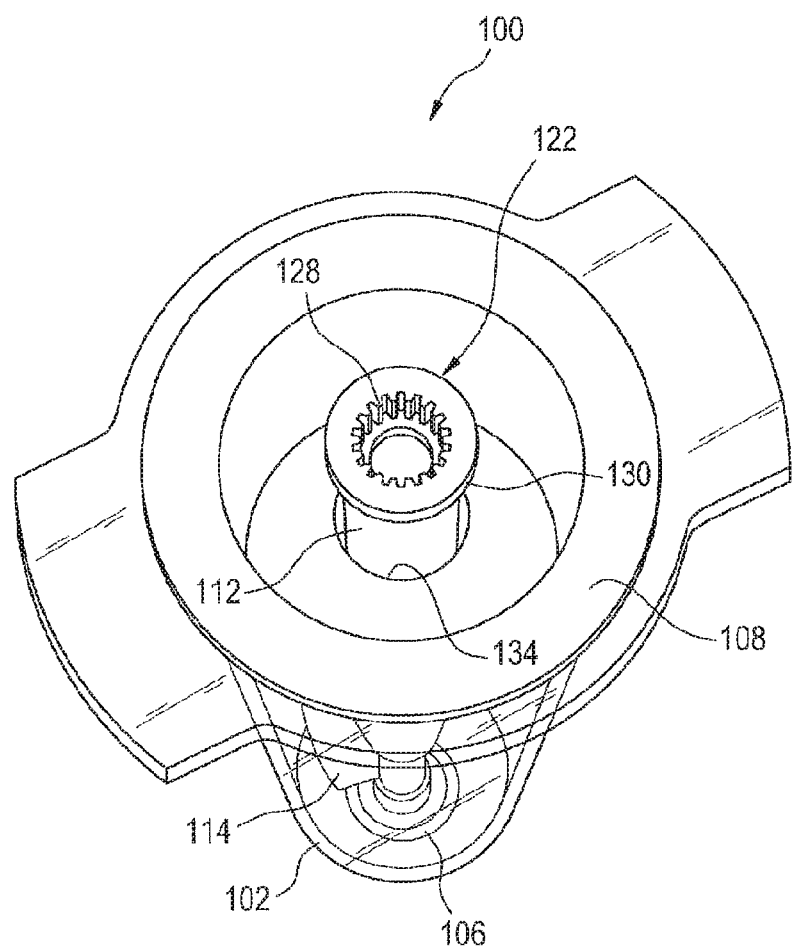
FIG. 4 is an illustration of a top section of a shaft in accordance with an embodiment of the present disclosure.

FIG. 4 shows an illustration of the cartridge 100 in a slightly tilted top view. As shown in FIG. 4, the shaft 112 projects out of an opening 134 of the cover 108. As described before herein, an adapter 122 is located in a top portion of the shaft 112. In this example the adapter 122 is designed such that an external driving assembly can transmit rotational power to the stirring assembly. To this end the adaptor 122 comprises a gear ring 128, which is typically designed such that it can form a close linkage with a suitable counterpart of the driving assembly. The adaptor 122 further comprises a flange 130. In accordance with an embodiment the flange 130 can be used to apply a force in axial direction onto the stirring assembly in order to move the stirring assembly from a first position to a second position and vice versa. For example, the part of the driving assembly to be connected with the adaptor 122 may comprise a U-shaped part, which can be put underneath the flange 130 thereby enabling the driving assembly to lift and lower the stirring assembly. If the first and second position of the stirring assembly are defined by corresponding angular ranges instead of an upper and lower position as described before herein, the flange 130 may be omitted.

Figure 5:
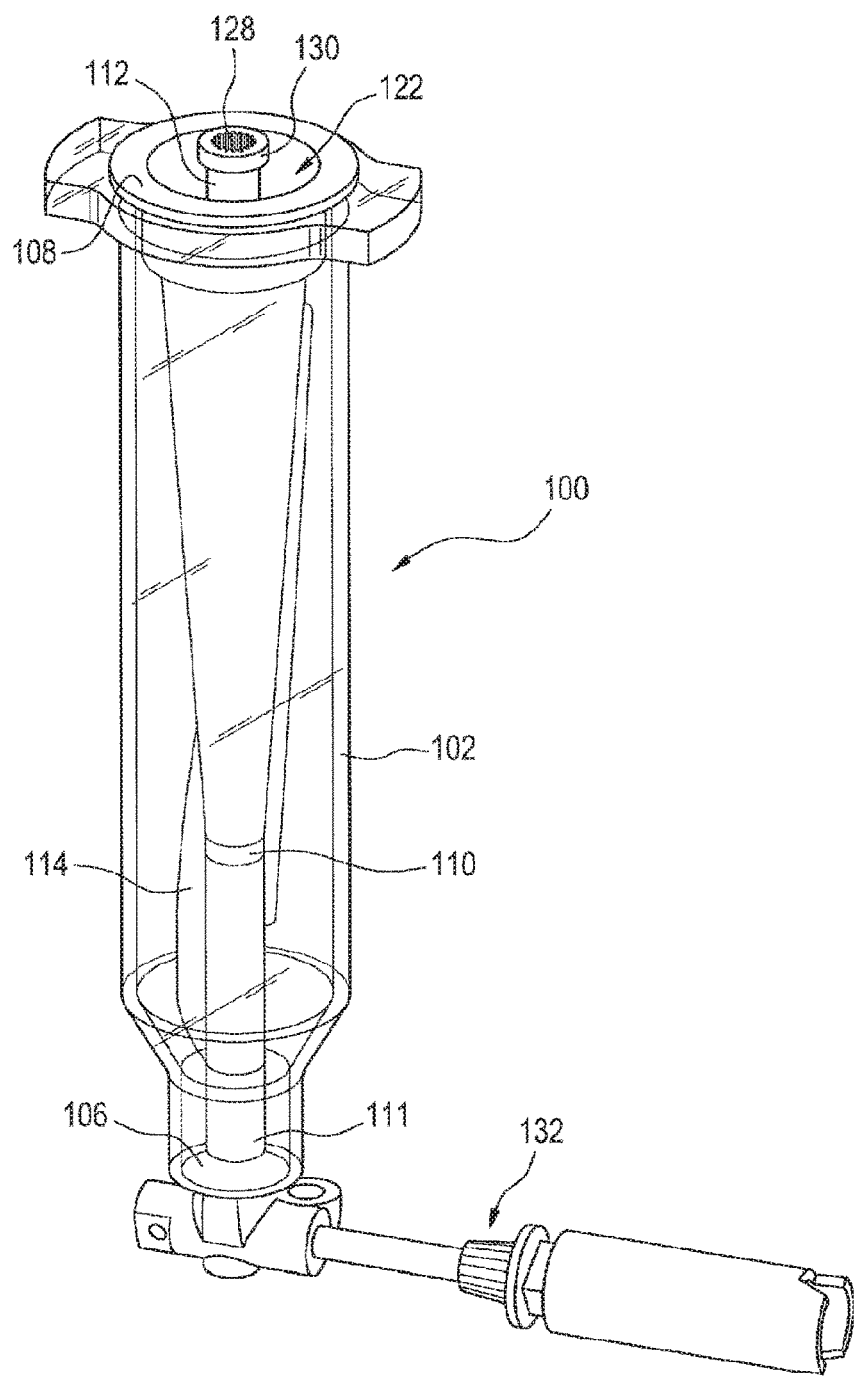
FIG. 5 is an illustration of a cartridge with a dispensing component attached in accordance with an embodiment of the present disclosure.

FIG. 5 is an illustration of a cartridge 100 with a dispenser component 132 attached to the fluid outlet 106 of the reservoir chamber 102. Once the stirring assembly has been moved to the second position the dispenser component 132 can be operated to draw a defined dispensing volume 116 from the cartridge for further use in the analysis procedure. The dispenser component 132 shown in FIG. 5 is merely for illustrative purposes. Other methods and components for dispensing fluid from the cartridge 100 also fall within the scope of the disclosure.

Figure 6:
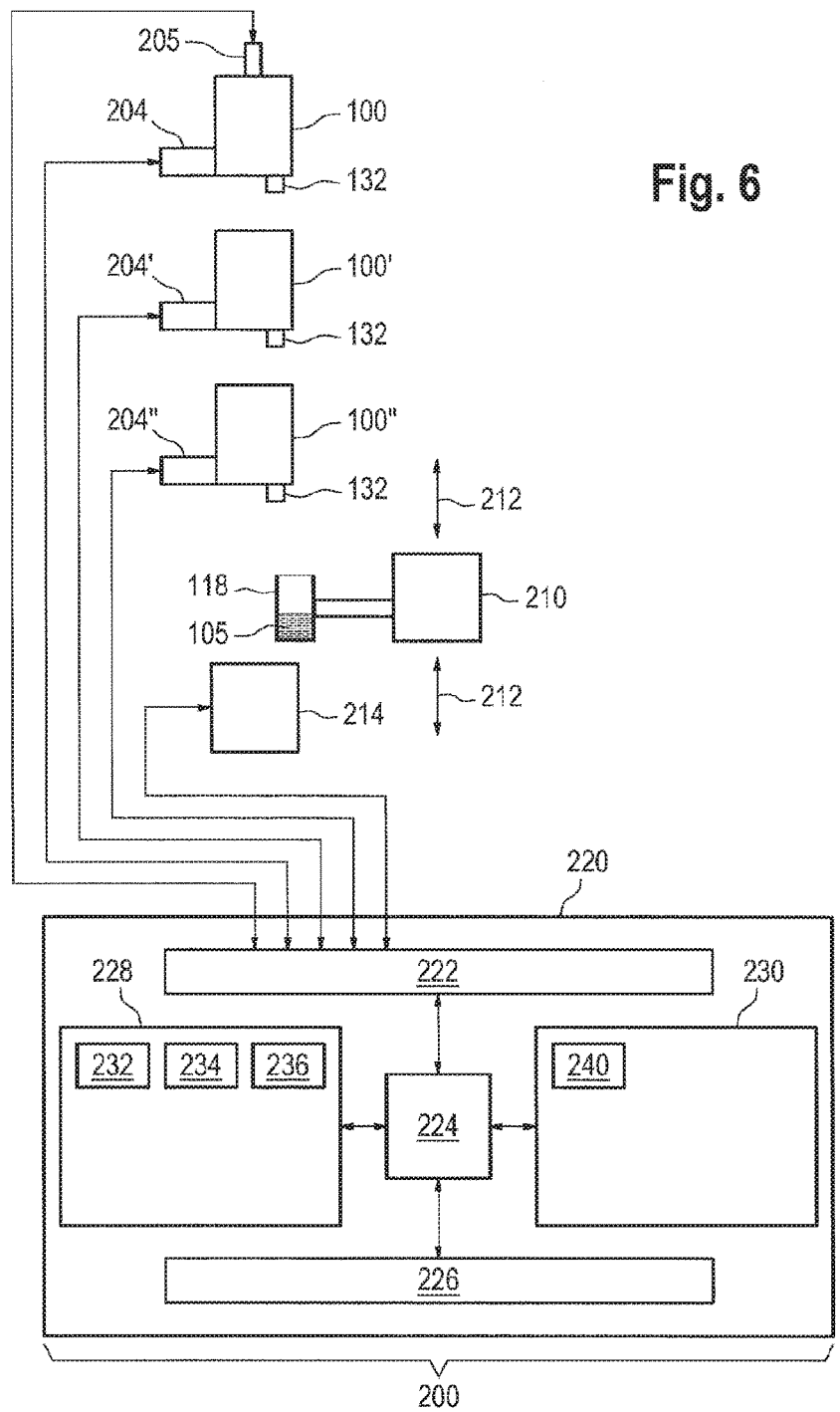
FIG. 6 is a block diagram of an automatic analyzer in accordance with an embodiment of the present disclosure.

FIG. 6 illustrates an example of an automatic analyzer 200. This automatic analyzer is shown as having three cartridges 100, 100' and 100". At least one of the cartridges, such as cartridge 100, contains the fluid 104 with suspended and partly sedimented particles in accordance with the examples of the FIGS. 1 to 5. The other cartridges 100' and 100" may be of identical or similar design and may contain fluids without sedimenting particles thus not requiring the stirring assembly of the embodiments illustrated in FIGS. 1 to 5.

There is an actuator assembly 204 connected to cartridge 100. There is an actuator assembly 204' attached to cartridge 100'. There is an actuator assembly 204" attached to cartridge 100". The actuators 204, 204', 204" are for actuating the dispenser 132 of the cartridges 100, 100', 100".

The automatic analyzer 200 is shown as having a relative movement means 210, which provides relative movement 212 between a receptacle 118 and the cartridges 100, 100' and 100". The receptacle 118 is shown as containing a biological sample 105. The cartridges 100, 100', 100" may be used to add one or more fluids to the biological sample 105. The automatic analyzer 200 may optionally comprise a measurement system 214. The measurement system 214 may comprise one or more sensors in order to determine the amount of a substance in the biological sample 105. For example, the measurement system 214 may comprise an NMR system, an optical transmission or reflectance measurement system, an electrochemical or optical sensor, a pH meter, a camera system or a chromatography system. The relative movement means 210 is also operable for moving the receptacle 118 to the measurement system 214.

The arrangement of the cartridges 100, 100', 100" and the measurement system 214 is representative. The measurement system 214 may be alternatively also a part of the receptacle 118. In some embodiments the receptacle 118 may remain in a fixed position and the cartridges 100, 100', 100" may move. The actuation systems 204, 204', 204" and the measurement system 214 are shown as being connected to a hardware interface 222 of a computer system 220. The computer system 220 functions as a controller for the automatic analyzer 200.

The computer 220 is further shown as containing a processor 224 that is configured to control the operation and function of the automatic analyzer 200 using the hardware interface 222. The processor 224 is shown as further being connected to a user interface 226, computer storage 228 and computer memory 230. The computer storage 228 is shown as containing an analysis request 232. The analysis request 232 contains a request to analyze the biological sample 105.

The computer storage 228 is shown as further containing sensor data 234 received from the measurement system 214.

The computer storage 228 is shown as further containing an analysis result 236, which was determined using the sensor data 234. The computer memory 230 contains a control module 240. The control module 240 contains computer executable code that enables the processor 224 to control the operation and function of the automatic analyzer 200. For instance, the control module 240 may use the analysis request 232 to generate commands to generate and send to the actuation systems 204, 204', 204", the measurement system 214 and the relative movement system 210. The control module 240 may also generate the analysis result 236 using the sensor data 234.

The automatic analyzer 200 has an additional driving assembly 205 that is coupled to the cartridge 100. The driving assembly 205 acts upon the stirring assembly of the cartridge 100. For example, the driving assembly 205 is configured to transmit rotational power onto the shaft 112 of the stirring assembly and/or to apply force onto the adapter 122 of the shaft 112 (cf., FIG. 4), thereby moving the stirring assembly between its first and second position (cf., FIG. 1A and FIG. 1B) if it receives a respective control signal from the control module 240. It is also possible to design the driving assembly 205 such that it can act upon the stirring assemblies of a plurality of cartridges 100, 100', and 100" simultaneously or be switched between the cartridges 100, 100' 100" by moving either the cartridges 100, 100', 100" or the driving assembly 205. Further, it is possible to implement a plurality of driving assemblies 205 acting upon a plurality of cartridges 100, 100', 100".

It should be noted that the cartridges 100, 100' and 100" are releasably held by the automatic analyzer 200 for convenient replacement if they are empty and for directly dispensing from the cartridges without pipetting.

In operation the automatic analyzer that holds the cartridges 100, 100' and 100" performs the following steps for analyzing the biological sample 105:

a. The computer system 220 controls the relative movement means 210 to place the receptacle 118 underneath the dispenser component 132 of the cartridge 100.
b. The computer system 220 controls the driving assembly 205 that is coupled to the adapter 122 of the shaft 112 to move the stirring assembly to its first position, thereby sealing the fluid outlet 106 of the cartridge 100.
c. The computer system 220 controls the driving assembly 205 to transmit a rotational power to the stirring assembly thereby stirring the fluid 104 contained in the reservoir chamber 102 such that microparticles comprised in the fluid 104 are resuspended. The stirring process may for example be conducted for a predetermined time period and with a predetermined rotational frequency applied to the stirrer 114.
d. The computer system 220 controls the driving assembly 205 to move the stirring assembly to its second position, thereby opening the fluid outlet 106 of the cartridge 100.
e. The actuator assembly 204 is controlled by the computer system 220 to act upon the dispenser 132 to dispense a required amount of the fluid 104 into the receptacle 118 for adding to and mixing with the biological sample 105.

In the following, the computer system 220 may control the relative movement means 210 to place the receptacle 118 under the dispensers 132 of the cartridges 100' and 100" for dispensing respective amounts of fluids from the cartridge 100' and 100" into the receptacle 118. Depending on the kind of analysis that is performed, such as an electrochemiluminescence analysis, incubation is performed before a measurement step that is executed by the measurement system 214 for determination of the presence of an analyte within the biological sample 105.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

LIST OF REFERENCE NUMERALS 100 cartridge
102 reservoir chamber
104 fluid
105 biological sample
106 fluid outlet
108 cover
110 first bearing
111 second bearing
112 shaft
114 stirrer
116 dispensing volume
118 receptacle
120 rotational axis
122 adapter
124 ventilation opening
126 ventilation channel
127 groove
128 gear ring
130 flange
132 dispenser component
134 opening
200 automatic analyzer
100' cartridge
100" cartridge
204 actuator assembly
204' actuator assembly
204" actuator assembly
205 driving assembly
210 relative movement means
212 relative movement
214 measurement system
220 computer
222 hardware interface
224 processor
226 user interface
228 computer storage
230 computer memory 232 analysis request
234 sensor data
236 analysis result
240 control module

What is claimed is:

1. A cartridge for dispensing a fluid, wherein the cartridge comprises:
    a reservoir chamber configured for receiving the fluid, the reservoir chamber having a fluid outlet, wherein the reservoir chamber further comprises a cover with a first bearing;
    a stirring assembly comprising a stirrer located inside the reservoir chamber, the stirring assembly further comprising a shaft, the shaft being connected to the stirrer, the shaft further being located at least partially inside the reservoir chamber and the shaft being configured to transmit rotational power to the stirrer, wherein
        the first bearing is formed by a first end of the stirring assembly and the cover, and wherein a second bearing is formed by a surface at a second end of the stirring assembly and a surface of the fluid outlet, and
        the stirring assembly is configured to be moved between a first position and a second position, wherein in the first position the stirring assembly is operable to seal the fluid outlet, the stirring assembly in the first position further being operable to form the second bearing with the fluid outlet such that the stirrer can be rotated about an axis defined by the first and second bearing, and wherein if the stirring assembly is in the second position the fluid can pass through the fluid outlet.

2. The cartridge of claim 1, wherein the reservoir chamber has an opening and wherein the cover is configured to seal the opening of the reservoir chamber, the cover having an opening configured to receive the shaft of the stirring assembly, wherein the cover and the opening extend along the shaft thereby forming an axially elongated radial bearing for the shaft.

3. The cartridge of claim 2, wherein the shaft of the stirring assembly projects through the opening of the cover.

4. The cartridge of claim 1, wherein the stirring assembly comprises a venting channel, the venting channel configured to form a first and a second opening when the stirring assembly is in its second position, wherein the first opening of the venting channel is located outside the reservoir chamber when the stirring assembly is in its second position, and wherein the second opening of the venting channel is located inside the reservoir chamber when the stirring assembly is in its second position.

5. The cartridge of claim 1, wherein the first position of the stirring assembly corresponds to a first axial position and/or a first angular range of the stirring assembly, and wherein the second position of the stirring assembly corresponds to a second axial position and/or a second angular range of the stirring assembly.

6. The cartridge of claim 1, wherein the stirrer is an Archimedean screw, a paddle mixer, a propeller mixer, a spiral stirrer, or an impeller mixer.

7. The cartridge of claim 1 further comprising a controllable dispenser component for dispensing a dispensing volume of the fluid from the reservoir chamber, the dispenser component being connected to the fluid outlet of the reservoir chamber.

8. The cartridge of claim 1, wherein the reservoir chamber is at least partly filled with the fluid, the fluid being a dispersion containing particles or a suspension containing particles.

9. The cartridge of claim 8, wherein the particles comprise any one of the following: magnetic beads, magnetized polystyrene beads, latex-beads, glass beads and combinations thereof, and/or wherein the particles comprise a coating for binding a biotinylated antibody or are antibody-coated.

10. The cartridge of claim 9, wherein the coating for binding a biotinylated antibody is streptavidine.

11. The cartridge of claim 1, wherein the shaft is configured to transmit rotational power from a driving assembly to the stirrer, thereby enabling the driving assembly to rotate the stirrer, the shaft is further configured to transmit a momentum from the driving assembly to the stirring assembly, thereby enabling the driving assembly to move the stirring assembly between the first and second position.

12. An automatic analyzer for analyzing a biological sample, the automatic analyzer comprising a holder for holding the cartridge according to claim 8, the automatic analyzer further comprising a first actuator assembly operable for actuating the controllable dispenser component for controlling the controllable dispenser component to dispense the dispensing volume of fluid from the cartridge, the automatic analyzer being operable to perform an analysis of the biological sample for detecting an analyte using the dispensing volume, the automatic analyzer further comprising a driving assembly configured to rotate the stirring assembly, and to move the stirring assembly between the first and the second position.

13. The automatic analyzer of claim 12, the automatic analyzer further comprising a controller, the controller being programmed to:
    control the driving assembly to move the stirring assembly to the first position,
    control the driving assembly to rotate the stirring assembly,
    control the driving assembly to move the stirring assembly to the second position,
    control the first actuator assembly to dispense the dispensing volume of the fluid.

14. A method for stirring and dispensing a fluid from a cartridge in accordance with claim 1, the method comprising:
    moving the stirring assembly to the first position,
    applying rotational power onto the shaft of the stirring assembly,
    moving the stirring assembly to the second position, and
    dispensing a dispensing volume of fluid from the cartridge.

* * * * *